Figure 1:
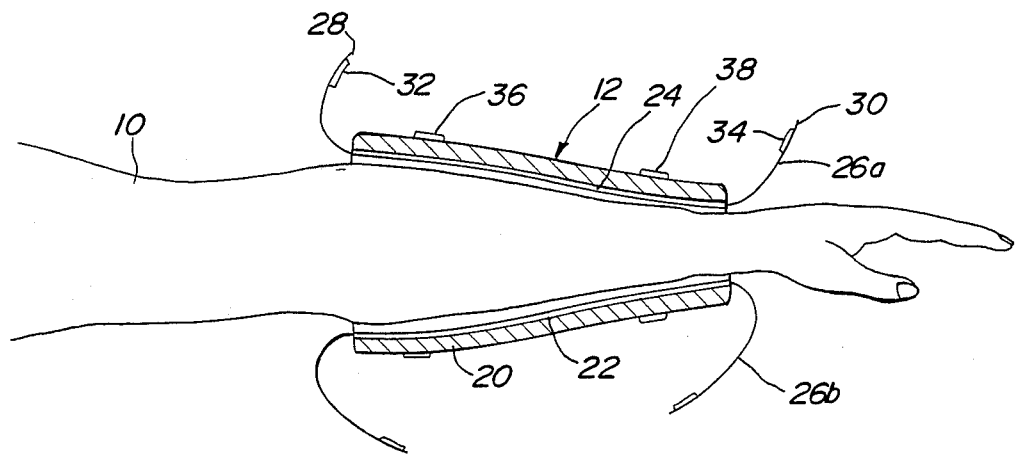

United States Patent [19]
Alper

[11] Patent Number: 4,945,903
[45] Date of Patent: Aug. 7, 1990

[54] ANTI-ITCH CAST

[76] Inventor: Max Alper, 3103 Greenfield Ave., Los Angeles, Calif. 90034

[21] Appl. No.: 345,003

[22] Filed: Apr. 28, 1989

[51] Int. Cl.$^5$ ............................................. A61H 11/00
[52] U.S. Cl. ................................. 128/91 R; 128/62 R; 128/63
[58] Field of Search .................. 128/62 R, 63, 65, 67, 128/90, 91 R, 91 A

[56] References Cited

U.S. PATENT DOCUMENTS

| | | | |
|---|---|---|---|
| 1,743,297 | 1/1930 | Wells | 128/62 R |
| 2,206,339 | 7/1940 | Ulman, Jr. | 128/91 A |
| 2,731,963 | 1/1956 | Blank | 128/82.1 |
| 2,807,815 | 10/1957 | Mack | 128/63 |
| 3,301,252 | 1/1967 | Mahoney, Jr. | 128/90 |
| 3,495,590 | 2/1970 | Zeiller | 128/91 A |
| 3,643,657 | 2/1972 | Whyte | 128/91 R |
| 3,720,205 | 3/1973 | Liebman | 128/63 |
| 3,800,789 | 4/1974 | Schloss | 128/90 |
| 3,826,252 | 7/1974 | Laico | 128/91 R |
| 3,882,857 | 5/1975 | Wood, Jr. | 128/90 |
| 3,906,943 | 9/1975 | Arluck | 128/90 |
| 3,959,841 | 6/1976 | Horne | 15/104.94 |
| 4,187,575 | 2/1980 | Collins | 128/63 |
| 4,235,228 | 11/1980 | Gaylord, Jr. | 128/91 R |
| 4,290,424 | 9/1981 | Wahl | 128/91 A |
| 4,306,549 | 12/1981 | Canie | 128/90 |
| 4,308,862 | 1/1982 | Kalmar | 128/91 R |
| 4,316,457 | 2/1982 | Liegeois | 128/90 |
| 4,479,490 | 10/1984 | Dedo | 128/91 R |
| 4,512,054 | 4/1985 | Clark | 128/63 |
| 4,577,622 | 3/1986 | Jennings | 128/67 |
| 4,600,618 | 7/1986 | Raychok, Jr. | 128/90 |
| 4,667,659 | 5/1987 | Hayday | 128/62 R |

FOREIGN PATENT DOCUMENTS 1404076  6/1988  U.S.S.R. ............... 128/62 R

*Primary Examiner*—Robert A. Hafer
*Assistant Examiner*—Michael Brown
*Attorney, Agent, or Firm*—Norton R. Townsley

[57] ABSTRACT

This invention concerns a device applied with a cast for immobilizing an injured limb. A comfort band is applied as a length of cotton tape or other flexible fabric material longitudinally of the limb with the ends of the tape protruding beyond the proximal and distal ends of the zone to be cast. The zone to be cast is then wrapped in an absorbent cotton mesh and padding is applied exteriorly of the mesh. The absorbent mesh and padding together form a cast building substrate. A settable cast forming material is applied to the substrate and allowed to set. Gripping the protruding ends of the comfort band allows movement of the comfort band in the space normally provided between the cast and limb to alleviate epidermal irritation.

3 Claims, 1 Drawing Sheet

ANTI-ITCH CAST

BACKGROUND

This invention relates to a cast for an injured limb.

Plaster and the like casts for supporting and immobilizing limbs remain on the limb for long periods to insure healing. A cast might be applied, for example, to a broken limb to support the bones as they knit and heal. Casts are also used to permit detached ligaments to reattach after corrective surgery. Because the cast remains in place for some time, discomfort can arise due to skin irritations which are inaccessible beneath the cast. This irritation can arise from normal itching which occurs from time to time on the skin. It can be especially irritating due to hair growth if the limb was shaved before application of the cast. Shaving is clinically necessary prior to surgery and is recommended before application of post-surgical as well as other casts.

A device for massaging the skin within a cast, splint, or like support is disclosed in U.S. Pat. No. 4,667,659, issued to Hayday. This device comprises a thin, plastic, elongated strip having a plurality of randomly spaced protrusions on one surface and a plurality of rounded indentations inset into the opposite surface. The device is insertable between the skin and cast in a space normally allowed for the flexing of muscles, the breathing of the skin and the circulation of air to dissipate heat.

Casts are typically formed by first enclosing the part of the limb to be immobilized in an absorbent cloth material. A padding such as cotton wool is next applied exteriorly of the cloth and a settable cast forming material is finally applied to the absorbent padding. The cast forming material is typically plaster of Paris or fiberglass. A coarse bandage is usually soaked in the plaster of Paris and wrapped about the padding to set with time and form the cast.

The cast must be sufficiently snug to immobilize the limb but loose enough to allow flexing of musculature in the immobilized area. Serious injury can result if the cast is applied too tightly. This can limit blood circulation in the affected area and cause permanent injury. Since the immobilized limb is enclosed, natural "breathing" of the epidermis cannot occur. Natural desquamation in which the outer epidermal layers are sloughed off from time to time is also inhibited. A build up of epidermal layers in the enclosed skin results. These factors exacerbate itching and irritation. Although patients do resort to the introduction of objects beneath the cast in an effort to alleviate irritation, most physicians strongly advise against this practice, recommending that the patient simply endures the discomfort. These foreign objects are not sterile, and can abrade or pierce the skin, resulting in infection.

Further, although a rigid object can sometimes reach an irritated area, this is not always possible. Areas can be inaccessible because of the configuration of the immobilized limb. In a cast for the entire arm, the forearm is generally immobilized at right angles to the upper arm. A rigid object can be introduced to scratch the forearm or regions of the upper arm but the elbow is typically inaccessible. In full leg casts, areas can be inaccessible simply because of the length of the cast. Even in shorter casts, it is difficult to remove epithelial cells sloughed off the skin or cast particles which result from normal deterioration of the cast with time.

It is accordingly desirable to provide a cast with which the above disadvantages associated with known arrangements are avoided or at least minimized.

SUMMARY

These and other needs and purposes are usefully addressed in the present invention by providing an anti-itch appliance useful with a cast for an injured limb. The cast typically has a cast building substrate that can comprise an absorbent cloth material for enclosing the zone to be immobilized and an absorbent padding exteriorly of the cloth. The cast also includes a settable material for forming the cast by application to the substrate in a flowable condition to set with time and form the cast. This invention is directed to a comfort band comprising an elongated length of material movably disposed adjacent to the skin and under the cast building substrate and extending longitudinally to protrude from both proximal and distal ends of the cast. Gripping the ends protruding from the cast allows movement of the comfort band in the normal space between the cast and the immobilized limb to alleviate epidermal irritation. Epidermal irritation is alleviated either by massage or by removing epithelial and cast materials from the space between the skin and cast.

The comfort band can comprise an elongated length of cotton tape. Preferably, the tape has a width in the range of about 0.5 to about 2 inches. Alternatively, the comfort band can be formed from a strip of polymeric plastic sheet material.

Securing or connecting means can be provided on the protruding ends to secure the band on the cast when not required for use. The securing means can comprise synthetic materials which adhere when pressed together, such as the material known and available under the trademark VELCRO. The comfort band can be of a length selected to permit the protruding ends to be connected to one another. Alternatively, zones of the appropriate type of connecting material such as VELCRO TM material can be applied to the exterior of the cast inward of its proximal and distal ends to allow a comfort band of a length selected to permit engagement of the protruding ends with the VELCRO TM material towards the respective ends of the cast.

A kit for forming a cast for an injured limb can include the comfort band. Such a kit can include (a) a cloth material for enclosing the portion of the limb to be immobilized, (b) an absorbent padding which, together with the cloth, comprises a cast building substrate, (c) a comfort band comprising an elongated length of material to be disposed beneath the cast building substrate and to extend longitudinally to protrude from both proximal and distal ends of the cast, and (d) a settable material for forming the cast by application to the substrate in a flowable condition for setting with time to form the cast.

Alternatively, the comfort band can be supplied by itself for use with any commercial cast forming product. The comfort band can be provided in an extra long length to be cut to size, and be provided with securing means for attaching the protruding ends of the comfort band onto the exterior of the cast. Appropriate securing means such as strips of VELCRO TM material can be used.

A method of installing a comfort band when forming a cast is also provided. The comfort band can be placed adjacent the skin before the cast is formed over it.

DRAWINGS

Figure 2:
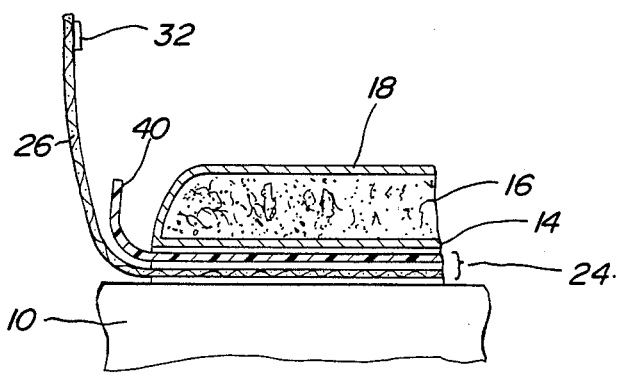

These and other features and advantages of this invention will become appreciated as the same becomes better understood with reference to the following description of a presently preferred embodiment of the invention, which description is presented by way of illustration only with reference to the accompanying drawings wherein:

FIG. 1 is a cross-sectional schematic view of one embodiment of a cast according to the invention applied to the forearm of a limb; and FIG. 2 is a detailed cross-sectional view of the proximal part of a cast according to an alternative embodiment of the invention.

DESCRIPTION

Referring to the drawings, an injured limb 10 to be immobilized is enclosed within a cast 12. The cast is generally formed in the conventional manner. Usually, the area of the limb to be enclosed in the cast 12 is shaved and a cotton mesh sleeve 14 is wrapped about the area to be enclosed in the cast. An absorbent padding material such as cotton wool 16 is then wrapped about the cotton sleeve. The mesh sleeve 14 and the cotton wool 16 serve as a cast building substrate. Finally, coarse gauze bandages 18 soaked in plaster of Paris or fiberglass with a water hardening resin are wrapped externally about the padding and allowed to set with time to form a composite cast.

The set cast has an exterior surface 20 and an interior surface 22. A space 24 aerated by the padding 16 is normally allowed between the interior surface 22 and the skin of limb 10. This space 24 accommodates swelling and allows a limited amount of play for flexing the muscles enclosed by the cast. The space 24 also permits a limited amount of air to circulate beneath the cast. However, because the skin enclosed by the cast cannot "breathe" normal and natural desquamation of the skin is inhibited, and thus irritation of the skin is inevitable.

At least one comfort band 26 is provided by the present invention in the space 24 between the cast and the limb. A sterile comfort band 26 is placed on the skin before the cast 12 is formed. While the cast is forming, the comfort band 26 can be held in place with adhesive tape beyond the anticipated boundaries of the cast.

Preferably, the comfort band 26 is made from a narrow strip of sterile cotton tape. The strip is in the range of between about 0.5 to about 2 inches in width. The band has a first proximal end 28 which protrudes from the proximal end of the space 24 and a second, distal end 30 protruding from the distal end of the space 24. Securing tabs 32 and 34 are provided or applied on or towards the proximal and distal ends of the comfort band respectively. The securing tabs are conveniently made from VELCRO brand securing material. Complimentary securing tabs 36 and 38 are provided or applied inwardly of the proximal and distal ends of the exterior surface 20 of the cast. The securing tabs can be formed from VELCRO material and have a pressure sensitive adhesive for attachment purposes, the adhesive being protected by removable paper. The VELCRO material at the respective ends of the cast and comfort band are complimentary to permit the protruding ends of the comfort band 26 to be secured on the cast for storage when not required for use.

The comfort band 26 allows massage or "scratching" of the skin enclosed within the cast by gripping the protruding ends of the band and moving it back and forth in the space 24 between the limb and the cast. As the cast is generally cylindrical, the comfort band may also be moved somewhat to rotate about the limb to alleviate circumferential irritation. A pair of comfort bands 26 are shown in the embodiment of FIG. 1. One such band 26a is located in the space 24 between the upper surface of the forearm and the cast 12. Another band 26b is disposed between the lower surface of the forearm and the interior surface 22 of the cast 12. Band 26a can thus be used to scratch or massage the skin on the top surface whereas band 26b can be used on the skin on the underside of the forearm.

The band 26 can be formed from a rough textured tape which provides an irregular surface to enhance the relief of irritation. Such a comfort band 26 not only permits relief from irritation but also massages the outer layers of the skin, thereby loosening the cells sloughed off during natural desquamation.

Since the comfort band 26 is made from tape, it is flexible and does not exhibit the disadvantages typically associated with rigid objects introduced into the space between the cast and limb. Rigid objects can snag on the skin, causing damage which can necessitate premature removal and replacement of the cast. A comfort band according to the invention is moreover advantageous in that it can be adapted to any cast irrespective of length or configuration. The comfort band of the invention accordingly allows relief from irritation with full leg and arm casts.

The cast of the invention is formed by first laying a comfort band 26 of a selected length longitudinally along the limb so that its ends will protrude from the cast. A cotton mesh sleeve 14 is then laid over the comfort band 26 and the limb 10 in the region to be enclosed. Padding in the form of cotton wool 16 is applied externally of the mesh 14 and a settable casting material such as plaster of Paris or fiberglass is finally applied to the padding and allowed to set with time.

The cotton mesh 14 and padding 16 together form a building substrate for the cast. Both the mesh and padding are absorbent. If plaster of Paris is used, it is typically applied in a flowable condition to coarse bandages 18 wrapped about the padding. Since the substrate is absorbent, the cast forming settable material may penetrate through the substrate to the comfort band. The comfort band preferably is absorbent and there is accordingly a possibility that the band might be incorporated into and form part of the cast when it sets. For this reason, it may be desirable to provide an impermeable layer on or between the surface of the comfort band and the cast. This layer can either be applied as a thin film on the tape itself or can, for example, comprise an elongated strip of plastic sheeting 40. Since plastic sheeting is impervious, the flowable casting material cannot penetrate the plastic. The band 26 is accordingly unaffected and can be withdrawn from the space 24 after the cast has set. This arrangement is illustrated in the embodiment shown in FIG. 2 of the drawings.

A comfort band kit is also provided according to the invention. The kit includes a comfort band 26 comprising an elongated length of cotton tape of a length selected to protrude from both proximal and distal ends of a cast with applicable securing tabs, i.e., VELCRO ™ fastening means. The cotton tape can be made oversized so it can be cut to length. One of the securing tabs can be pre-applied to one end of the tape, i.e., the end that is not cut.

The kit can also include means for forming a cast such as an absorbent cotton mesh for surrounding the limb and padding for forming a cast building substrate. The kit can further include a settable material to permit a cast to be formed in the field. Such a kit may be useful to medics in the field in military applications or to physicians in emergency situations.

The comfort band 26 of the kit preferably includes securing means on at least one end with a tab of complimentary VELCRO brand material separately supplied to allow one end of the band to be secured to the exterior surface of the cast. For adaptability, the comfort band 26 can be supplied as a roll of tape for use with a cast of indeterminate dimensions. Alternatively, a number of bands 26 of different lengths with securing means on opposite ends can be provided. A comfort 26 band of a length selected to protrude from the cast to be formed in the field would be used when using the latter kit.

The comfort band 26 of the invention is also useful in providing means of introducing soothing lotions or talcum powder into the space 24. It can also be used to introduce rubbing alcohol or deodorant interiorly of the cast. Of course, where necessary, and as shown in FIG. 1, more than one comfort band may be provided somewhat circumferentially about the limb when forming the cast. A comfort band according to the invention thus allows relief from irritation of the skin enclosed by the cast in a safe, simple and yet effective manner.

Although the invention has been described and illustrated with reference to a presently preferred embodiment, it will be apparent to those skilled in the art that many variations and modifications would be possible without departing from the scope of the appended claims. In one example, one end of a comfort band which has been in use for some time may be attached to the end of a fresh band and the connected bands drawn through the space 17. When the used band has been fully withdrawn, the comfort bands may be separated so that a fresh band is placed in the cast. This process would also assist in removing particulate matter from the space 17 and perform a cleansing operation similar to that performed by a "pull through" in cleaning a rifle. In addition, this invention is not limited to use with plaster of Paris casts, but can be used with a cast made of substantially any material.

Therefore the scope of the appended claims should not necessarily be limited to the description of the preferred versions described herein.

What is claimed is:

1. A device for protecting an injured body part comprising:
   (a) a cast having a proximal and a distal end and an exterior, surrounding said injured body part; and
   (b) a comfort band comprising an elongated length of flexible material having a proximal and a distal end, movably disposed adjacent to said injured body part and beneath said cast and protruding longitudinally from both proximal and distal ends of said cast, wherein gripping said proximal and distal ends of said comfort band allows movement of said comfort band beneath said cast to alleviate epidermal irritation;
   said comfort band having securing means on said proximal and distal ends for storing said comfort band on said cast when said comfort band is not in use,
   said means for securing being synthetic material that adheres together when pressed together.

2. The device of claim 1 in which said comfort band is sufficiently long so that said proximal and distal ends can be connected to one another.

3. The device of claim 1 further including means for securing on said exterior surface inward of said proximal and distal ends of said cast, and wherein said comfort band is of a length selected for the engagement of said proximal and distal ends of said comfort band with said means for securing towards said respective proximal and distal ends of said cast.

* * * * *